United States Patent [19]

Beall

[11] Patent Number: 4,693,255

[45] Date of Patent: Sep. 15, 1987

[54] MEDICAL APPARATUS METHOD FOR ASSESSING THE SEVERITY OF CERTAIN SKIN TRAUMAS

[76] Inventor: Harry C. Beall, 1008 Horton Rd., Durham, N.C. 27704

[21] Appl. No.: 726,015

[22] Filed: Apr. 22, 1985

[51] Int. Cl.$^4$ .............................................. A61B 5/00
[52] U.S. Cl. ..................................... 128/654; 128/665
[58] Field of Search ............... 128/653, 654, 659, 664, 128/665, 633; 378/100, 99; 358/105, 111

[56] References Cited

U.S. PATENT DOCUMENTS

| | | | |
|---|---|---|---|
| 3,483,565 | 12/1969 | Jaffe et al. ........................ | 128/659 |
| 4,029,085 | 6/1977 | DeWitt et al. . | |
| 4,170,987 | 10/1979 | Anselmo et al. . | |
| 4,178,917 | 12/1979 | Shapiro . | |
| 4,218,703 | 8/1980 | Netravali et al. .................. | 358/105 |
| 4,398,213 | 8/1983 | Haendle et al. .................... | 358/111 |
| 4,436,095 | 3/1984 | Kruger . | |
| 4,444,196 | 4/1984 | Stein . | |
| 4,459,990 | 7/1984 | Barnea . | |
| 4,464,789 | 8/1984 | Sternberg ........................... | 358/105 |
| 4,515,165 | 5/1985 | Carroll .............................. | 128/664 |
| 4,536,790 | 8/1985 | Kruger et al. ..................... | 378/99 |
| 4,581,635 | 4/1986 | Franke .............................. | 378/99 |

FOREIGN PATENT DOCUMENTS

| | | | |
|---|---|---|---|
| 0019478 | 11/1980 | European Pat. Off. ............. | 128/665 |
| 1138113 | 2/1985 | U.S.S.R. ............................. | 128/665 |

OTHER PUBLICATIONS

AGA Thermovision Brochure, Oct. 1971.
Edrich et al, "Focusing Long-Wave Thermography", Microwave Power Symposium, 1979, Jun. 11-15, pp. 266-267.
Proc. Soc. Exp. Biol. Med., 133: 1384-1387, "Simple Method for Quantitation of Enhanced Vascular Permeability" by Udaka et al.

Primary Examiner—William E. Kamm
Assistant Examiner—Ruth S. Smith
Attorney, Agent, or Firm—Richard E. Jenkins

[57] ABSTRACT

An objective medical analysis system for assessing the severity of traumas to human skin, particularly for objectively analyzing the degrees of burns to human skin, utilizing computerized analysis of a video recording of the kinetics of the change in appearance of the traumatized skin site and the generation of a two-dimensional color-coded map on an associated video monitor for diagnostic use by the physician. Specifically relating to burns, the system utilizes computerized analysis of a video recording of the kinetics of the appearance of a tracer dye within a burn site and subsequently generates a color-coded two-dimensional video map of the human skin burn site with differentiation between untraumatized normal skin and first degree, second degree, and third degree burns for use to aid the physician in burn diagnosis.

8 Claims, 3 Drawing Figures

MEDICAL APPARATUS METHOD FOR ASSESSING THE SEVERITY OF CERTAIN SKIN TRAUMAS

DESCRIPTION

1. Technical Field

This invention relates to a new apparatus and method for assessing the severity of traumas to human skin. Even more specifically, the invention particularly relates to computerized analysis of a set of video images which record the kinetics of the appearance of dye color within a burn site during a brief time period subsequent to intravenous injection of a tracer dye in order to aid the physician in more effectively diagnosing the severity of the burn to the human skin.

2. Background Art

The use of various types of dye tracer tests for burn classification have been well known for a number of years. The dyes utilized have included Evans Blue dye, Pat. Blue dye, Brompheonol Blue dye, Fluorescein Dye, Sulphan Blue Dye and tetracycline. However, virtually all of the dye tracer tests relied on subjective monitoring of the extent of the dye staining of the human skin burn area. It is not believed that any technology was available until now for quantitatively recording and analyzing the kinetics of the dye staining within the burn area over a predetermined time period.

Color photography has previously been used to document the clinical progress of staining by Pat. Blue V dye about burn areas at specific times (1, 2, 5 and 10 minutes) after intravenous dye injection at 4 to 72 hours after the burn event and the limits of the staining then compared with the fate of the burns at the time of slough or evaluated by biopsy if immediate excision was performed. It was found that the dye color fully developed within normal unburned skin in 10 minutes following dye injection and that full thickness burns did not accept the dye at all. Injured, but viable, skin concentrated the dye so that the second degree burn area was more deeply colored by the dye than the uninjured skin. The clear delineation between relatively unstained third degree burn areas and well stained partial thickness second degree burn areas remained distinct for at least 20 minutes. Over the course of several hours the color of the dye gradually stained the nonviable third degree burn areas.

Other prior art studies and publications confirm that an intravenously injected dye produces an eventual staining pattern within the traumatized skin tissue about 12 hours after the intravenous injection of the dye that is radically different from the pattern which is observed during the initial flush of the dye into the trauma area in the first 20 minutes after the dye injection. These prior tests suggest that the kinetics of dye influx within the first 20 minutes after the dye is intravenously administered has significant analytical value for distinguishing partial thickness from full thickness burns and that this dependent variable of the dye test has not been fully appreciated or exploited heretofore as a medically significant indicator of the severity of the burn.

Of specific interest to the present invention, U.S. Pat. No. 4,170,987 discloses a skin diagnosis system and method particularly adapted to diagnose the degree of burn to skin tissue. Light is reflected from each incremental area (pixel) of the skin and directed simultaneously through three separate color bandpass filters in order to produce three analog signals which are directly related to the intrinsic reflectance of the light of the three different wavelengths. The three analog signals are simultaneously, for each skin pixel as it is scanned, converted into digital numbers by three analog-to-digital converters and, after subsequent electronic processing, fed to a color television monitor to produce a visual false color display of the scanned skin on a real-time basis. Thus, the skin may be scanned at predetermined times during the critical time period of interest and a series of hard color prints produced from the visual color display of the monitor which can be utilized by a diagnosing physician to detect color changes which may assist to determine different depths and degrees of burns.

U.S. Pat. No. 4,459,990 relates to a digital radiographic method and apparatus for the visualization of a portion of the circulatory system of a subject. The patent teaches the feeding of a catheter through a blood vessel of the subject while exposing the subject's body to radiation from a radiation source and detecting the radiation at the opposite side of the subject with a device which converts the x-ray image to a light image. The patent describes processing of the signal from the detector successively through a TV camera, analog-to-digital converter, digital processor and ultimately a video display unit. An associated memory circuit serves to provide a display of all prior visits of the catheter and a display of the blood vessel and its junctures along with a display of the current position of the catheter.

Also of possible interest, U.S. Pat. No. 4,436,095 discloses a method and apparatus for generating video images of the internal structure of the body wherein a contrast medium is injected into the body vessel and x-ray radiation directed at the body which is detected and converted into an electronic video signal. The analog video signal is processed by comparing the video signal level at each pixel of a new frame with the video signal level at the corresponding pixel of the stored preceeding frame and selecting and re-storing at each of said pixels the lower of the two video signal levels being compared. In this fashion, the stored video frame is dynamically processed to retain at each pixel a video signal level that represents the highest opacity to radiation during the video processing period and which can be displayed and recorded on associated video display and recording equipment.

In summary, it is believed that prior burn diagnosis apparatus and methods inevitably result in a relatively subjective and inaccurate analysis of the severity of the burn to the tissue. Furthermore, known video analysis systems used in other unrelated medical procedures do not lend themselves to analysis of traumas to the skin tissue including burns. It is believed that the new apparatus and method of the invention meets the need for a system which provides for objective analysis to assess the severity of traumas including burns to human skin tissue.

DISCLOSURE OF INVENTION

The present invention is directed to a new apparatus and method for assessing the severity of traumas, including burns, to the human skin. Non-burn traumas may include those related to skin grafting, tumors, and antigen inoculations for allergy testing. The new apparatus and method is based on objective analysis of the kinetics of the change in skin appearance following a trauma thereto. More particularly, the invention is intended to objectively analyze the rate of appearance of a tracer dye within the burn site during a brief time period subsequent to an intravenous injection of a tracer dye. The invention records the rate and pattern of dye appearance within the burn area with a black and white television camera and simultaneously produces a video recording thereof.

Selected frames of the video signal are processed through a video analog-to-digital converter and are thereby converted into digital data which are stored in the memory of the analog-to-digital converter or other suitable memory means. Thereafter, the recorded digital video data is analyzed by computerized image analysis which generates a two-dimensional pseudocolor display of the video digital data which serves as a color-coded map of the severity of the burn within the field of view of the television camera during the time period of the tracer dye test. It should be noted that the video digital data processing and analysis preferably is done at a remote location from a burn patient's room. If so, only the television camera and video recorder are required to be brought into the patient's room and the bulky processing and analyzation equipment may be kept in a separate remote location. This results in more convenience in the use of the apparatus of the invention and reduces risk of infection to a patient who may be in a sterile site.

The computer may be a conventional personal computer such as the IBM-PC which is programmed in a conventional manner known to one skilled in the computer art so that the program thereof will determine the rate at which the tracer dye appears at discrete sites, called pixels, within the burn area during the first 20 minutes of the dye tracer test. This is accomplished by having the computer analyze digital data derived from a predetermined and preselected number of sequential frames from the video recording on a pixel by pixel analysis. The numerical values of the rates are then classified by the computer into a plurality of categories with each category being assigned a pseudocolor code. In this fashion, the kinetic rates are then mapped by the computer into a pseudocolor two-dimensional pixel array and displayed on an electrically associated video screen as a computer-generated pseudocolor image which may be used by the physician in his diagnosis of the skin burn severity. It is further contemplated that the resulting two-dimensional pseudocolor map on the color video screen may be photographed with a color camera to produce a hard print or, in the alternative, a hard print may be created by an electrically associated ink jet color printer.

Therefore, it is a primary object of the present invention to provide a new objective method for the analysis of certain trauma to the skin.

Another object of the invention is to provide a new method to assist the physician in his diagnosis of skin tissue burns by providing for heretofore unavailable objective analysis of burn severity.

A further object of the invention is to provide a method for generating an accurate and reliable color-coded two-dimensional map of a human skin burn with highly objective differentiation between normal skin and first, second, and third degree burn areas.

Further features and advantages of the invention will become more readily apparent from the following detailed description when taken in conjunction with the accompanying drawings.

BEST MODE FOR CARRYING OUT THE INVENTION

The invention can be generally described as an apparatus and method for objectively assessing the severity of burns to human skin by analyzing the dynamic staining pattern to the burn site by intravenously introduced dyes.

Figure 1:
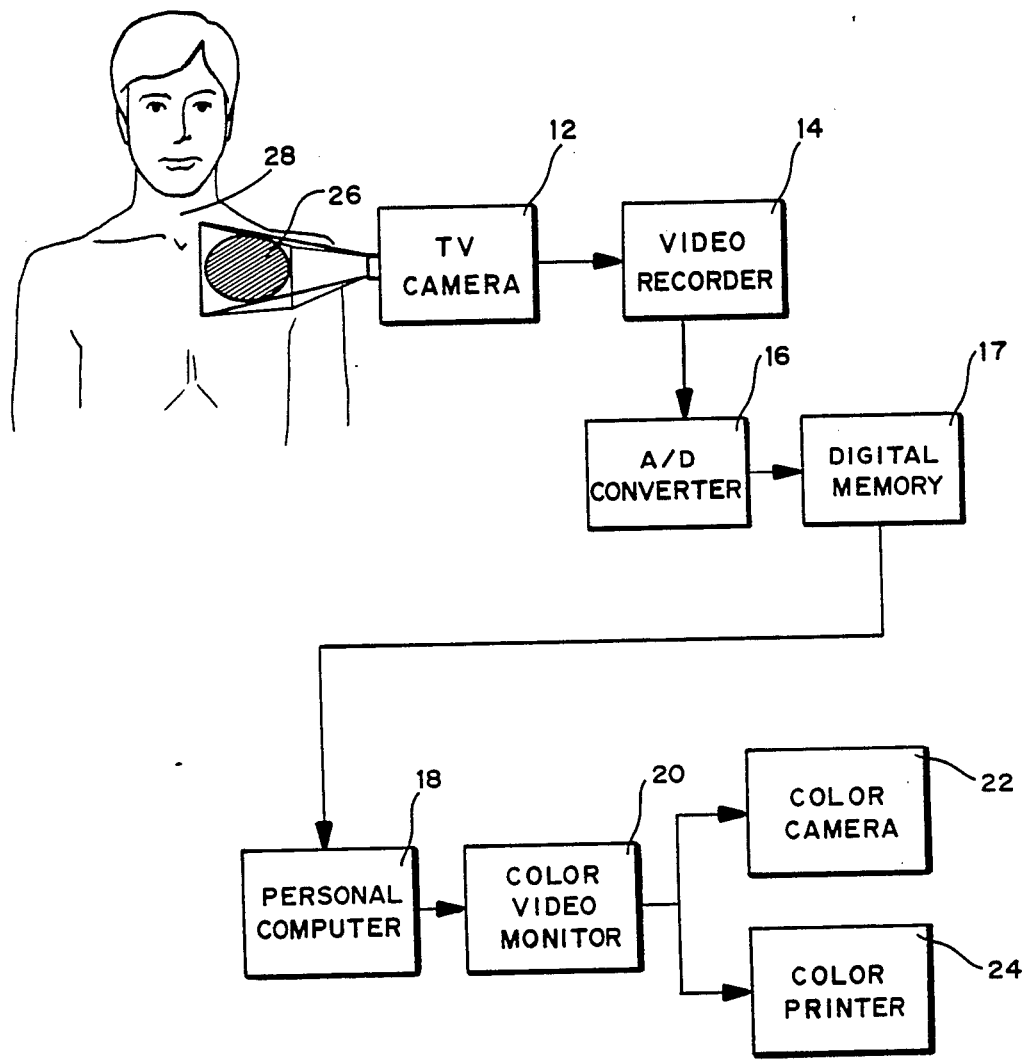
FIG. 1 is a general block diagram useful in explaining the basic features of the present invention.

The apparatus of the invention (see FIG. 1) for objective analysis of burn severity utilizing the known procedure of the dye tracer test preferably comprises a black and white television camera 12 with an electrically connected video recorder 14. Video recorded 14 is also electrically connected with an analog-to-digital converter 16 of the conventional type now known which are capable of digitizing 256 or more points along each horizontal scan line of a typical TV signal during the occurrence of a single frame of a video signal and are available as a plug-in accessory board for the IBM-PC and other personal computers. Analog-to-digtal converter or video digitizer 16 is electrically connected to personal computer 18, preferably an IBM-PC personal computer or IBM-compatible personal computer with a hard disk drive. Finally, personal computer 18 is electrically connected to a conventional color video monitor 20 for displaying the two-dimensional pseudocolor mapping of the skin burn area generated by personal computer 18.

Optionally, a photographic color camera 22 may be utilized to take a hard print photograph of color video monitor 20 or a color printer 24 may be electrically connected with personal computer 18 to make a hard paper print of the computer generated image on the color video monitor 20. It is to be understood that this particular system with conventionally programmed software for personal computer 18 is provided in order to objectively analyze the dye stain pattern of a skin burn 26 to a patient 28 after intravenous injection of a tracer dye.

In order to facilitate better understanding of the functioning of the invention, the preferred procedure for the use of the aforementioned apparatus to analyze a skin tissue burn site will now be fully described.

In operation, the invention first requires that patient 28 having burn trauma 26 to a portion of skin be immobilized and receive an intravenous injection of a tracer dye preferably Brompheonol Blue or Fluorescein. The patient remains motionless during the 20 minutes immediately following the injection and the appearance of the tracer dye in burn site 26 is recorded by means of black and white television camera 12 and electrically connected video recorder 14. When a flourescent dye such as Flourescein is used, an appropriate excitation filter must be mounted on an illumination light and an appropriate barrier filter mounted on the camera lens in order to properly record the flourescence of the dye. It should be understood that the video recording documents the intensity variations due to the influx of the dye, and the video format provides for preserving the data as a two-dimensional video image. Video recorder 14 can stop at any selected point on the recorded tape and display a static video image of a single frame of the video record for at least several minutes.

Preferably in a location remote from the patient's room in view of convenience and patient safety considerations, the analog signal from video recorder 14 is digitized by video analog-to-digital converter 16 which breaks up each line of the analog video signal and samples the signal at a fixed number of discrete data points. Video recorder 14 may be the unit originally used in conjunction with camera 12 or another unit into which the recorded tape is placed. The amplitude of the video signal is determined at each sample point by analog-to-digital converter 16 and all digital samples are stored as sets of digital data in ordered arrays in digital memory 17 of analog-to-digital converter 16 or in other suitable memory means. It is preferred that at least five static images from the sequence of the video record of the first ten minutes of the video recording of the dye tracer test be selected, digitized and recorded by analog-to-digital recorder 16. After recorder 16 has completed this function, the data sets are transferred to the memory, preferably a hard disk, of electrically connected personal computer 18.

The next step of the invention comprises computer processing of the stored digital data in a procedure that systematically compares corresponding digital samples, or pixels, from at least five arrays of stored digital data that represent the five digitized video frames. The computer is programmed so as to compare the five sets of digital data from the five video frames on a pixel by pixel basis and then to calculate through the use of an appropriate algorithm a rate of change of each set of corresponding pixels of the video images. The calculated rates are then stored in the original two-dimensional pixel order within a new digital array within the computer's memory. This new array represents the set of calculated rates of change for each pixel element of the five selected successive video frames from the first twenty minute segment of the video recording. The numerical values of the rates of change of the pixel elements represent the rates of influx of tracer dye during the dye tracer test.

It should be pointed out that there is a physiological basis for the fact that the dye will appear in the video images with essentially three different rates:
(1) the most rapid rate being the second degree burn areas which are partial thickness burns;
(2) the intermediate dye influx rate being that of normal skin;
(3) the slowest rate of dye influx being within areas of full thickness second and third degree burns.

These observations are from physiological tests with animals which have conclusively proven these phenomena. These phenomena are also believed to be true with respect to humans.

Computer 18 next generates a two-dimensional map of the burn area 26 and its immediate surrounding tissue. The algorithm of the computer program constructs the two-dimensional mapping by classifying the numerical value of the rate of change array into eight major categories. Each of the eight categories is represented by one pseudocolor display color so that the display on monitor 20 of all pseudocolor pixel elements in their proper two-dimensional orientation results in a two-dimensional eight color pseudocolor mapping of burn area 26 and immediately surrounding tissue. The map is now displayed on electrically connected video monitor 20 so that the physician may analyze the contrasting colors within the map in order to quantitatively and objectively determine the severity of burn 26 by noting the clustered appearance of pixels of corresponding color and then referencing the pseudocolor legend in order to determine the relative severity of each portion of the burn. It is also contemplated that the invention may include the final step of permanently recording the color map on video monitor 20 by either color photography with color camera 22 or a color printout from electrically connected color ink jet printer 24.

Figure 2:
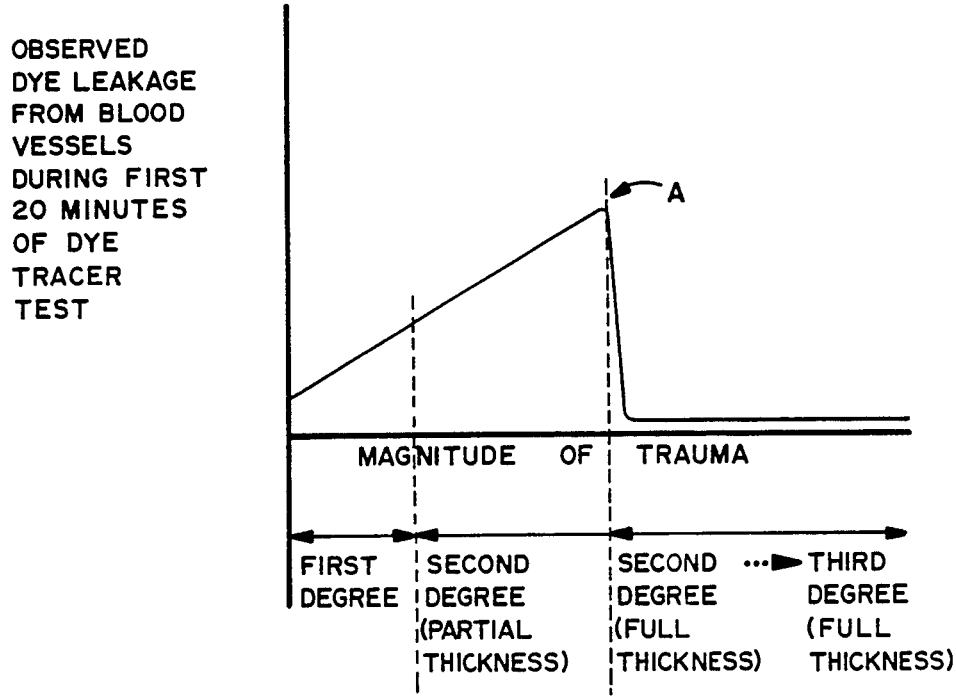
FIG. 2 is a plot of dye leakage from blood vessels during dye tracer test versus magnitude of skin trauma.

To more fully appreciate the instant invention, it must be understood that the previously known dye tracer test can be used as an accurate indicator of burn severity only if the data from the test are accurately recorded and analyzed in an objective form such as provided by the present invention. A better understanding of the aforementioned physiological basis for the dye tracer test can be found by a close study of FIG. 2 of the drawings wherein the results of a tracer dye test are plotted as dye leakage from blood vessels during the first 20 minutes after intravenous injection versus the severity of the skin injury. The plot of FIG. 2 is drawn as a linear function for convenience although the precise shape may vary from case to case. The plot represents the physiological reality that extrinsic dye leakage from blood vessels will increase with the severity of the burn up to a point at which the vasculature of the burn area is damaged so severely that no dye can be transported by blood flow. The very low amplitude of the plot to the right of infection point A indicates that third degree and full thickness second degree burns do not become significantly stained during the initial 20 minutes of the tracer dye test.

Figure 3:
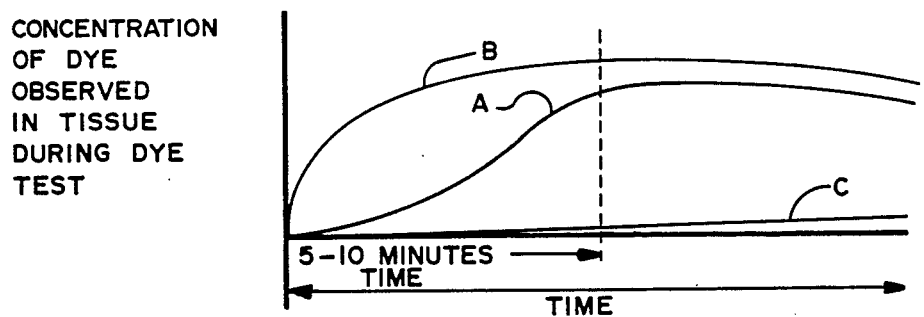
FIG. 3 is a plot of dye magnitude observed in tissue versus duration of dye test.

When the magnitude of dye observed in burned tissue is plotted as a function of time another set of factors appear in the kinetic data which is best represented by FIG. 3. As can be seen, three sets of representative data are plotted in FIG. 3. Plot A represents the expected kinetics of the appearance of the extrinsic dye within normal untraumatized skin. Untraumatized skin is purposefully observed in order to form a base line for observations regarding traumatized skin. It can be seen that the initial portion of A forms an approximately exponential curve indicating that during the initial time period the tracer dye is being injected and mixing within the blood volume. Plot A reaches its peak within about 5 to 10 minutes following the intravenous injection of the tracer dye and then begins a slow decline that may last from about 12 to 24 hours. Within the traumatized tissue represented by plot B the color of the tracer dye appears more rapidly than the color of the tracer dye in the normal skin represented by plot A. The intensity of the tracer dye color may eventually peak at a value significantly greater than the color intensity of the normal skin for reasons including the following:
(1) the tracer dye leaks from the tissue vasculature at a much higher rate;
(2) the dye accumulates within the trauma area; and
(3) the first and second degree burn areas may be more translucent than normal skin.

It should further be appreciated that in FIG. 3 plots A and B are normalized to the same amplitude for diagramatic purposes and that only one representative plot B has been drawn for both first degree and second degree partial thickness burns. According to the severity of burn areas within these two classifications plot B may exhibit relatively steeper or more shallow initial slope, but the shape of the latter portion of plot B would be expected to be quite similar in both cases.

Plot C of FIG. 3 represents the full thickness burn areas of a third degree burn and is shown as slowly rising in amplitude with time. The initial rise only begins slowly during the first 20 minute period recorded in the practice of the subject invention. It should be appreciated that plot C eventually peaks within about 24 hours.

In conclusion, the subject invention provides a heretofore unavailable apparatus and method for accurate and objective analysis of the severity of traumas to the skin, particularly burns. This will enable surgeons to more readily diagnose the burn and excise the necrotic skin of major burns and thereby prevent bacterial infection of the body which is a major cause of death in burn victims. The inability to accurately assess the exact margins of nonviable tissue has heretofore discouraged many surgeons from attempting early excision of necrotic skin and resulted in the reliance on the more traditional treatment to burn victims.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method of objective analysis of the condition of traumatized surface tissue of a patient, comprising the steps of:
    introducing a tracer dye into the patient;
    scanning the surface area of said traumatized surface tissue with a television camera for about 1–20 minutes after introduction of the dye to detect the rate of non-reflective perceptible extrinsic changes in the surface area due to the initial appearance of the dye;
    recording analog signals from the television camera on a video recorder;
    digitizing a pre-selected plurality of static images on the video recording and storing the digitized data for each of said plurality of images in an electronic memory;
    computer processing of the digitized signals by systematically comparing consecutive corresponding digital data from the stored digital data representing the plurality of static images and calculating the rate of change of surface area appearance of corresponding sections of surface area of the plurality of static images and then storing the new digital data;
    computer generating a two-dimensional map of the traumatized surface tissue by first assigning a color code to each of a predetermined plurality of change rates and then generating a two-dimensional color coded mapping of the traumatized surface tissue with each color representing an assigned change rate; and
    displaying the two-dimensional color coded map of the traumatized surface tissue on a color display monitor.

2. A method as described in claim 1 including the step of making permanent color photographic prints of selected images on the color display monitor.

3. A method as described in claim 1 including the step of making permanent color print-outs of selected images on the color display monitor with a color printer.

4. A method as described in claim 1 wherein the computer constructs the map by classifying the numerical values of the rate of change data into eight categories and then assigning a pseudocolor to each of the categories so that the resulting two-dimensional map comprises eight pseudocolors within the traumatized surface tissue area wherein each color represents a different rate of change.

5. A method of objective analysis of the severity of a burn to surface tissue of a patient, comprising the steps of:
    introducing a tracer dye into the patient;
    scanning the surface area of the burned surface tissue with a television camera for about 1–20 minutes after introduction of the dye to detect the rate of non-reflective perceptible extrinsic changes in the surface area due to the initial appearance of the dye within the burn area;
    recording analog signals from the television camera on a video recorder adapted to stop at selected points on a recorded tape and to display a static image of a singular frame of the video record;
    digitizing a pre-selected plurality of static images on the video recording and storing the digitized data for each of said plurality of images in an electronic memory;
    computer processing of the digitized signals by systematically comparing consecutive corresponding digital data from the stored digital data representing the plurality of static images and calculating the rate of change of surface area appearance of corresponding sections of surface area of the plurality of static images and then storing the new digital data;
    computer generating a two-dimensional map of the burn area by assigning a color code to each of a predetermined plurality of change rates and generating a two-dimensional color coded mapping of the burn area with each color representing an assigned change rate; and
    displaying the two-dimensional color coded map of the burn area on a color display monitor.

6. A method as described in claim 5 including the step of making permanent color photographic prints of selected images on the color display monitor.

7. A method as described in claim 5 including the step of making permanent color print-outs of selected images on the color display monitor with a color printer.

8. A method as described in claim 5 wherein the tracer dye is intravenously injected into the patient.

* * * * *